United States Patent [19]
Hessel et al.

[11] Patent Number: 5,135,497
[45] Date of Patent: Aug. 4, 1992

[54] LARGE VOLUME PRESSURIZED FLUID DISPENSER

[75] Inventors: Steve Hessel, Fountain Valley; Gil Jemmott, San Marcos; William C. Brown, Huntington Beach, all of Calif.

[73] Assignee: Baxter International Inc., Deerfield, Ill.

[21] Appl. No.: 726,481

[22] Filed: Jul. 8, 1991

[51] Int. Cl.⁵ .......................................... A61M 37/00
[52] U.S. Cl. ............................ 604/132; 128/DIG. 12; 222/94; 222/95; 222/214
[58] Field of Search ............... 604/131, 132, 133, 134; 128/DIG. 12; 222/211, 212, 214, 386.5, 94, 95, 97, 100, 103, 104; 239/323

[56] References Cited

U.S. PATENT DOCUMENTS

| | | |
|---|---|---|
| 3,412,906 | 11/1968 | Dinger . |
| 3,469,578 | 9/1969 | Bierman . |
| 3,486,539 | 12/1969 | Jacuzzi . |
| 3,506,005 | 4/1970 | Gilio et al. .......................... 604/132 |
| 3,698,595 | 10/1972 | Gortz et al. . |
| 3,767,078 | 10/1973 | Gortz et al. . |
| 3,796,356 | 3/1974 | Venus, Jr. .......................... 222/212 |
| 3,876,115 | 4/1975 | Venus, Jr. et al. . |
| 3,883,046 | 5/1975 | Thompson et al. ............... 222/386.5 |
| 3,961,725 | 6/1976 | Clark ................................ 222/386.5 |
| 4,140,117 | 2/1979 | Buckles et al. . |
| 4,201,207 | 5/1980 | Buckles et al. . |
| 4,215,689 | 8/1980 | Akiyama et al. . |
| 4,318,400 | 3/1982 | Peery et al. . |
| 4,386,929 | 6/1983 | Peery et al. . |
| 4,419,096 | 12/1983 | Leeper et al. ..................... 222/386.5 |
| 4,666,430 | 5/1987 | Brown et al. . |
| 4,702,397 | 10/1987 | Gortz ................................. 222/211 |
| 4,741,733 | 5/1988 | Winchell et al. . |
| 4,813,937 | 3/1989 | Vaillancourt . |
| 4,915,693 | 4/1990 | Hessel ............................... 604/132 |
| 4,953,753 | 9/1990 | Gortz ................................. 222/212 |
| 4,968,301 | 11/1990 | diPalma ............................. 604/132 |

Primary Examiner—Gene Mancene
Assistant Examiner—Michael Lynch
Attorney, Agent, or Firm—Paul E. Schaafsma; Amy L. H. Rockwell; Paul C. Flattery

[57] ABSTRACT

The present invention provides housing containing a cylindrical, prestress member around which an elongated elastomeric bladder is wrapped. This interior of the bladder defines a fluid chamber. A filling port and an exit port are provided in fluid communication with the fluid chamber to provide for filling and dispensing of the liquid. The elongated bladder is wrapped around the cylindrical, prestress member so that the bladder is prestressed in the axial direction when disposed thereon.

13 Claims, 5 Drawing Sheets

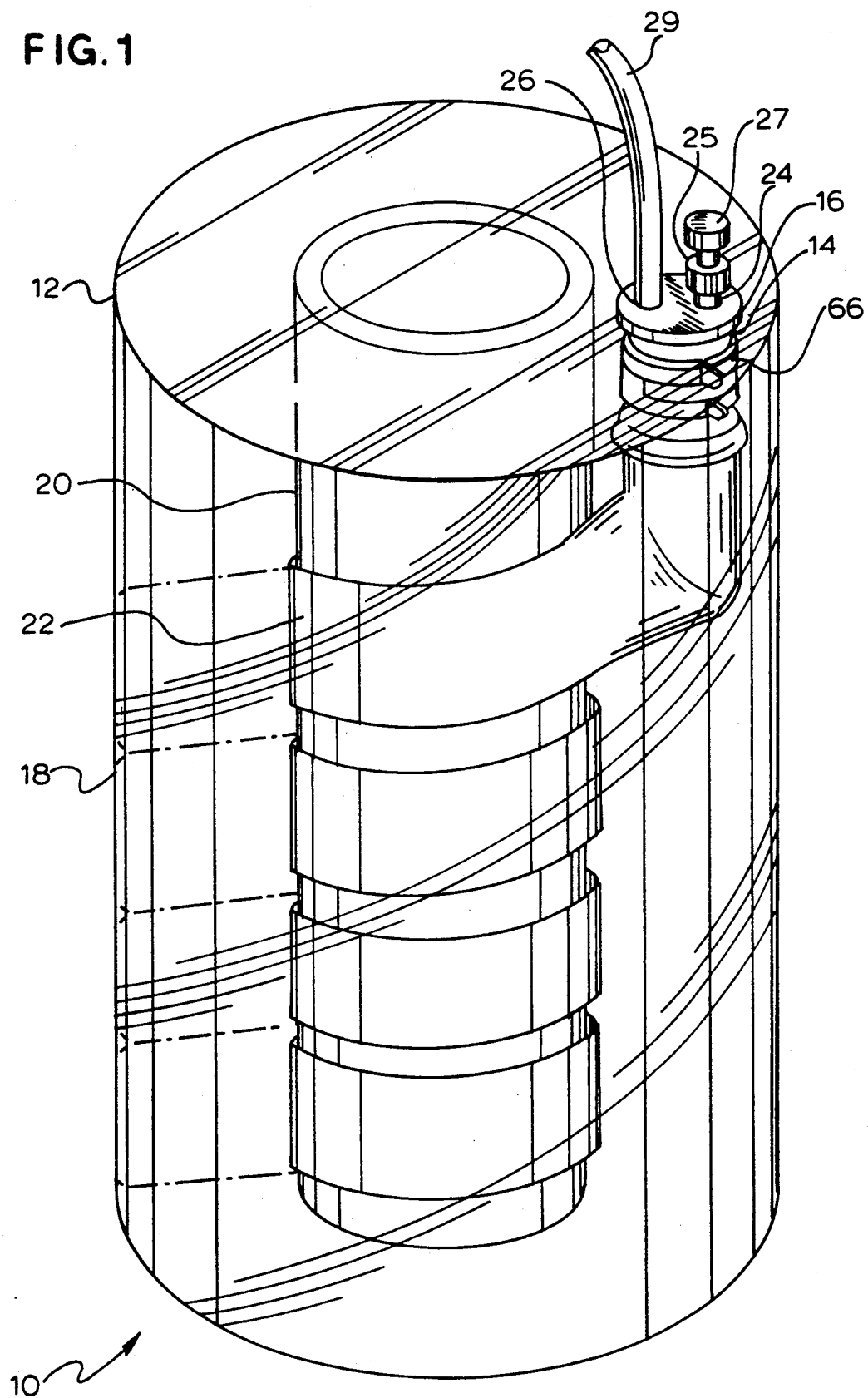

LARGE VOLUME PRESSURIZED FLUID DISPENSER

FIELD OF THE INVENTION

The present invention relates to the controlled delivery of fluids, and, in particular, to portable apparatus for delivery of a large volume of a beneficial agent to a patient.

BACKGROUND OF THE INVENTION

Devices for infusing to a patient a beneficial agent such as a drug diffused in a medical liquid are known in the art. The most common type of such device utilizes an elevated glass or flexible container having the beneficial agent diffused in a medical liquid which is fed by gravity to a patient's venous system via a length of flexible plastic tubing and a catheter. The rate of flow in this type of device is commonly regulated by an adjustable clamp on the tubing. This type of infusion suffers from the drawback of requiring a relatively stationary patient and is dependent on the height differential between the source of liquid and the patient for accurate delivery rates.

Another type of infusion device utilizes electromechanical components in a pump to provide fluid propulsion of the liquid for infusion into the patient. Such electronically controlled infusion devices, however, suffer from several drawbacks including the cost of such electrical components as well as the limit such electrical components and the necessary power source place on the size and thus portability of the device.

Devices in the art are also utilized which employ an elastomeric bladder which contains the liquid to be infused under pressure for infusion. Such elastomeric bladder infusion devices are seen in Winchell et al. U.S. Pat. No. 4,741,733 and Hessel U.S. Pat. No. 4,769,008, both of which are assigned to the assignee of the present invention.

While elastomeric bladder infusion devices such as seen in the Hessel and Winchell et al. patents provide an accurate flow of the liquid being infused over an extended period of time, the amount of liquid to be infused is limited by the size of the devices. While simply utilizing a larger bladder and a resultant larger housing would provide more liquid to be infused, such devices would be exceedingly large. Additionally, if the liquid to be infused is stored in a frozen state, an excessive amount of time would be required to thaw the liquid prior to dispensing because of the small surface area of the liquid.

What would thus be desirable would be an infusion device capable of containing a large amount of liquid to be infused which would not be exceedingly large to carry. Additionally, the infusor should store the liquid to be infused in a manner which, when frozen, is easy to thaw. Finally, such device should not be cost prohibitive. The present invention meets these requirements.

SUMMARY OF THE INVENTION

The present invention provides an elastomeric bladder infusion pump capable of storing a large amount of liquid to be infused. The present invention provides housing containing a cylindrical, prestress member around which an elongated elastomeric bladder is wrapped. This interior of the bladder defines a fluid chamber. A filling port and an exit port are provided in fluid communication with the fluid chamber to provide for filling and dispensing of the liquid. The elongated bladder is wrapped around the cylindrical, prestress member so that the bladder is prestressed in the axial direction when disposed thereon.

By utilizing an elongated elastomeric bladder, a large amount of surface area of the liquid exists which aids in thawing frozen liquid. Additionally, the helically wrapped elastomeric bladder utilizes more of the internal volume of the housing than a comparable spherical shaped bladder, thereby reducing the size of the device.

BRIEF DESCRIPTION OF THE DRAWINGS

FIG. 1 is a perspective view of an embodiment of an infusion device made in accordance with the principles of the present invention;

DETAILED DESCRIPTION OF THE PRESENTLY PREFERRED EMBODIMENT

Figure 3:
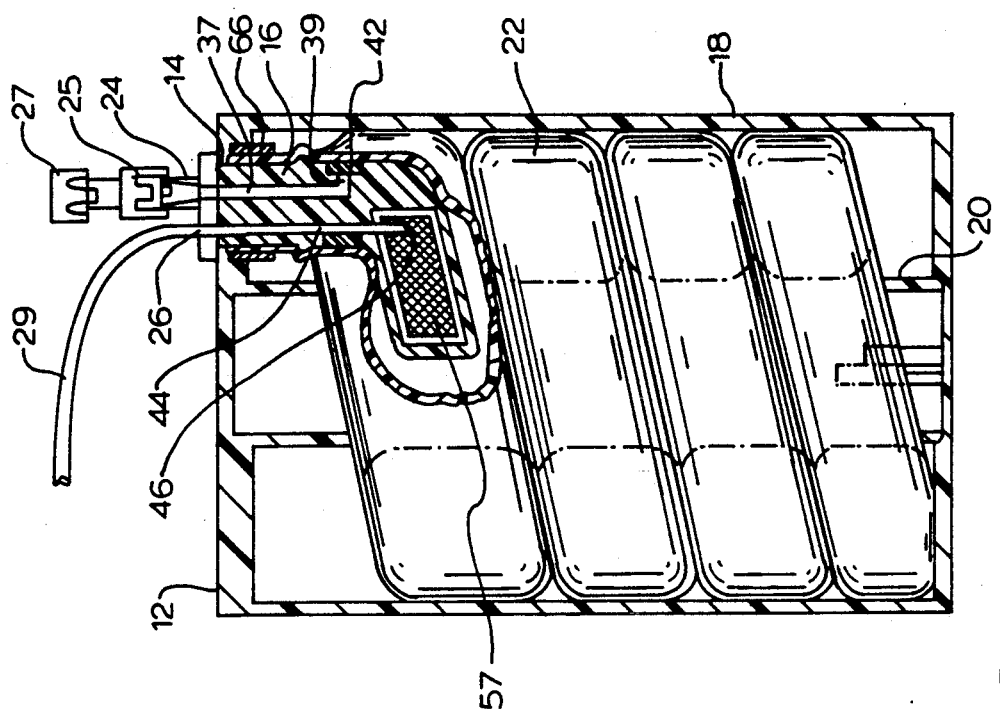
FIG. 3 is an elevational, partially sectional view of the device of FIG. 1 with the elongated elastomeric bladder in a filled state.

Referring to FIG. 1, an elastomeric bladder infusion device made in accordance with the principles of the present invention is designated generally by the reference numeral 10. The device includes a casing 12 which can be formed from any of a variety of known thermal distortion moldable polymeric materials such as acrylic or styrene, which protects the material of the bladder from ultraviolet light yet is substantially transparent to visible light to permit visual observation of the internal components.

Casing 12 is provided having an opening 14 at the proximal end thereof for receiving access housing 16. The exterior of casing 12 or access housing 16 preferably includes a vent to prevent internal pressurization of contained air. Casing 12 includes an external, generally cylindrical wall 18 and an internal, generally cylindrical prestress member 20. Wrapped around the internal prestress member 20 is an elongated bladder 22 as will be described in more detail below.

Provided in the proximal opening is the access housing 16. The access housing 16 includes a filling port 24 and an exit port 26 at the proximal end thereof. The filling port 24 can preferably be provided with a female luer for connection to a filling apparatus. A double luer cap 25 can be provided which has a male luer for engagement with the female luer on the filling port 24, and a female luer for engagement with a male luer cap 27. When the male luer cap 27 is removed for filling the bladder 22, the double luer cap 25 remains aseptic and may be detached from the female luer of the fill port for sealing the fill port. Alternatively, the double luer may be aseptically sealed with a sealing membrane. The sealing membrane may be removed at the time of filling and, after filling, the filling port 24 may be sealed with the male luer cap 27.

Figure 2:
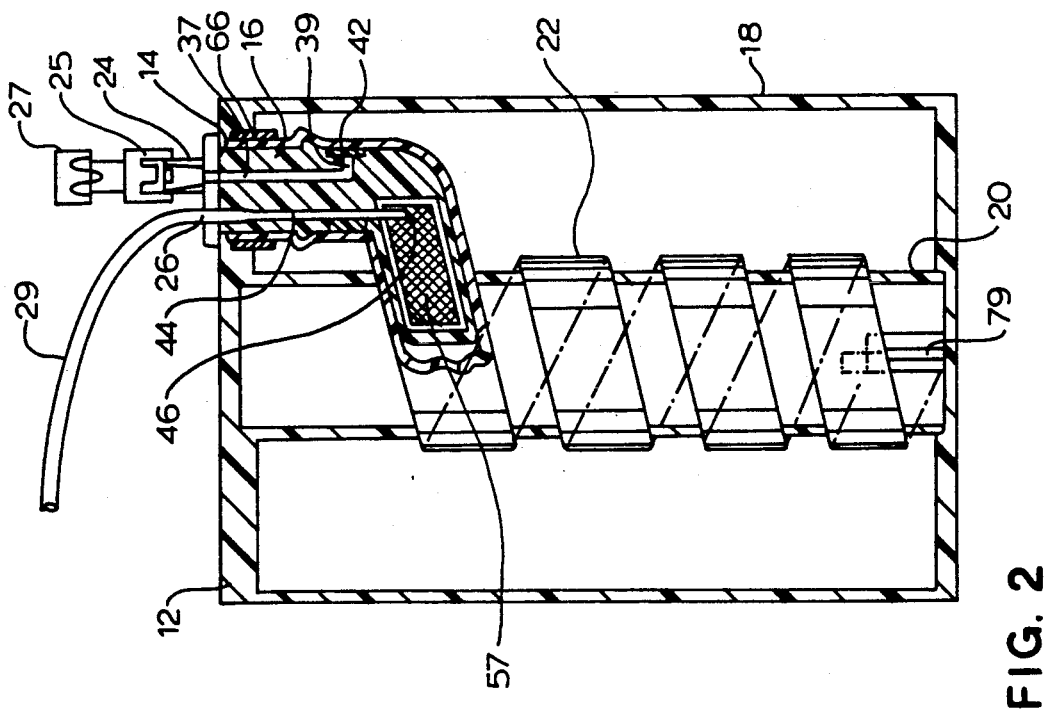
FIG. 2 is an elevational, partially sectional view of the device of FIG. 1 with the elongated elastomeric bladder in an unfilled state.

Sealingly attached to the exit port 26 is conventional I.V. tubing 29. The tubing 29 is secured at its proximal end to a tubing seat 31 provided in the exit port 26. The distal end of the tubing 29 is connected to a rigid plastic housing by adhesive or the like. The rigid plastic housing can preferably include a luer connector for connection to a catheter to be inserted into the patient's venous system. In a first preferred embodiment, the rigid plastic housing can also include a flow regulator such as a glass capillary flow regulator as seen and described in U.S. Pat. No. 4,741,733 entitled "INFUSOR HAVING A DISTAL FLOW REGULATOR", the disclosure of which is incorporated herein by this reference. Finally, a conventional tubing clamp can be provided on the tubing 29 which will be normally clamped during catheterization. Referring now to FIG. 2, an elevated, partially sectional view of the device 10 is seen in which the elastomeric bladder 22 is unfilled. The access housing 16 is contained in the proximal opening 14 in the casing 12. The access housing 16 may be produced in accordance with known thermoplastic forming techniques and can preferably comprise acrylic, styrene or any other rigid thermoplastic material that is substantially inert in the environment of the intended pharmaceutically active material. If it is desirable from a manufacturing standpoint, the access housing 16 may be formed from other materials and thereafter be provided with a continuous coating of an appropriate inert substance.

The elastomeric bladder 22 includes an interior which defines a fluid chamber. The filling port 24 of the access housing 16 is in fluid communication with the fluid chamber by way of an influent lumen 37 and a transverse influent duct 39 (best seen in FIG. 4). Backflow of the liquid in the elastomeric bladder 22 out of the transverse influent duct 39 is prevented by a one-way valve. The one-way valve includes an elastic valve band 42 disposed coaxially about the access housing 16 and in overlapping engagement with the transverse influent duct 39. The access housing 16 is preferably provided with an annular recess for receiving the valve band 42 so that the outside diameter of the valve band 42 is substantially the same as the diameter of the adjacent portions of the access housing 16.

Pressure from an influent stream through transverse influent duct 39 will cause momentary displacement of elastic valve band 42 to permit the influent stream to pass into the interior of the elastomeric bladder 22. Upon termination of the influent stream, valve band 42 will elastically return to sealingly obstruct influent duct 39, thereby preventing leakage of material from the fluid chamber back out through the transverse influent duct 39. Alternatively, the filling port 24 can include an elastomeric septum capable of being punctured by a sharp cannula to fill the bladder and resealable upon withdrawal of the cannula.

The exit port 31 is also in fluid communication with the fluid chamber by way of effluent lumen 44 and transverse effluent duct 46. While in a preferred embodiment, the flow regulator can be contained in rigid housing at the distal end of the tubing 29, in an alternate embodiment, the effluent lumen 44 is provided with a flow regulator 48 which may again comprise a glass capillary tube, stainless steel tube or other suitable embodiment. The flow regulator 48 regulates in a controlled manner the effluent stream against the pressure developed from the elastomeric bladder 22. Use of this flow regulator is described in detail in U.S. Pat. No. 4,769,008 to Hessel, the disclosure of which is incorporated herein by this reference.

The flow regulator 48 can be secured within effluent lumen 44 by an adhesive material or a preformed member 51. The adhesive material or preformed member 51 provides sealing engagement between the walls of the effluent lumen 44 and the outside diameter of the flow regulator 48 to avoid any fluid communication around the outside of the flow regulator 48.

The access housing 16 can be further provided with an access port 53 which allows exposure of the flow regulator 48 extending through the effluent lumen 44 for receiving a quantity of the adhesive material 51 such as a urethane based UV-cured epoxy or other material that will be chemically inert in the presence of the pharmaceutically active material contained within the elastomeric bladder 22. The adhesive material 51 not only secures the flow regulator 48 but also seals the access port 53.

Further contained on the access housing is a screen or mesh 57 which traverses effluent duct 46 and welded in place. The screen or mesh 57 precludes introduction into the patient of any solid matter such as pharmaceutical material that may have become crystallized during storage. The screen or mesh 57 may be made of stainless steel, platinum wire, or other suitable material or any of a variety of polymers such as polytetrafluoroethylene having a porous or multifilament configuration capable of operating as a screen, and which will be substantially unreactive in the presence of the pharmaceutical material. The porous size of the screen or mesh 57 should be large enough so that the sum of the flow paths through the mesh or screen 57 will permit sufficient flow that the mesh or screen will not be a factor in the overall flow rate of the device. The access housing 16 may be provided with a shallow depression for receiving the screen or mesh 57 such that the outside diameter of the screen or mesh 57 is substantially the same as the diameter of the adjacent portions of the access housing 16.

Figure 4:
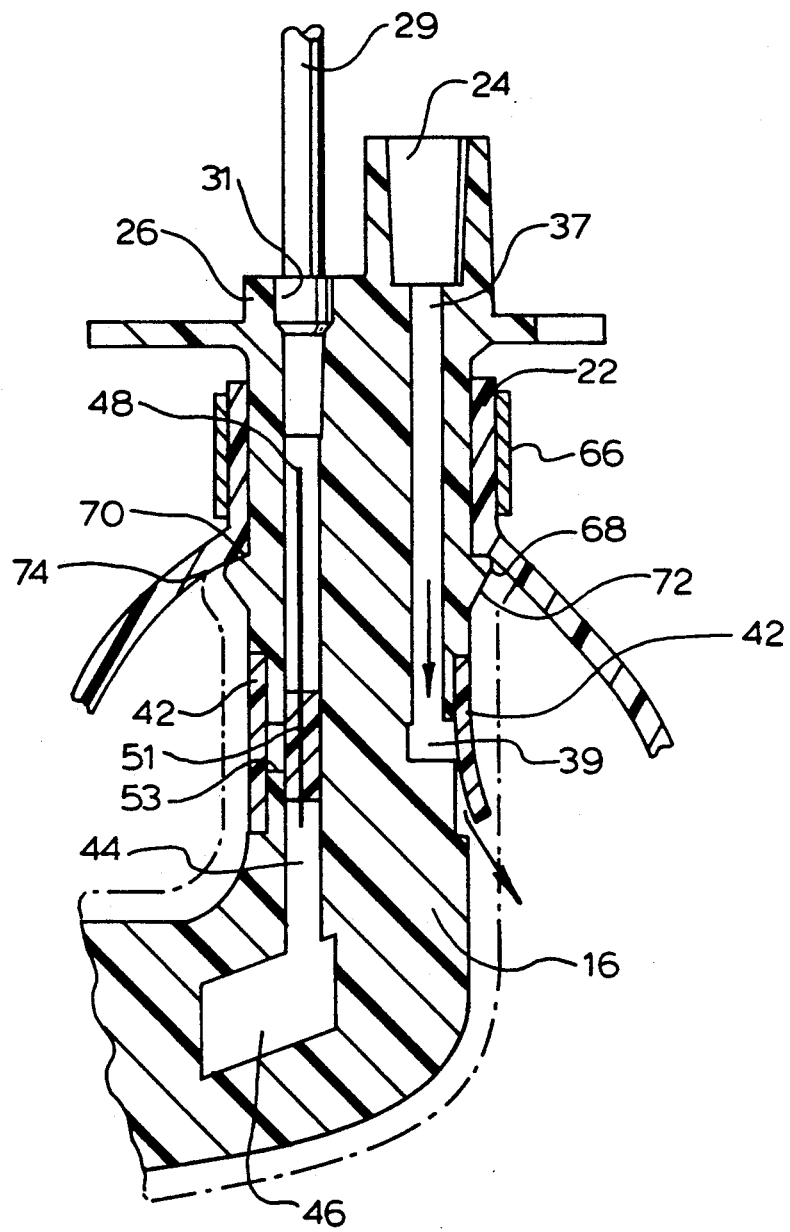
FIG. 4 is an elevational cross-sectional view of the access housing of the device of FIG. 1.
Figure 5:
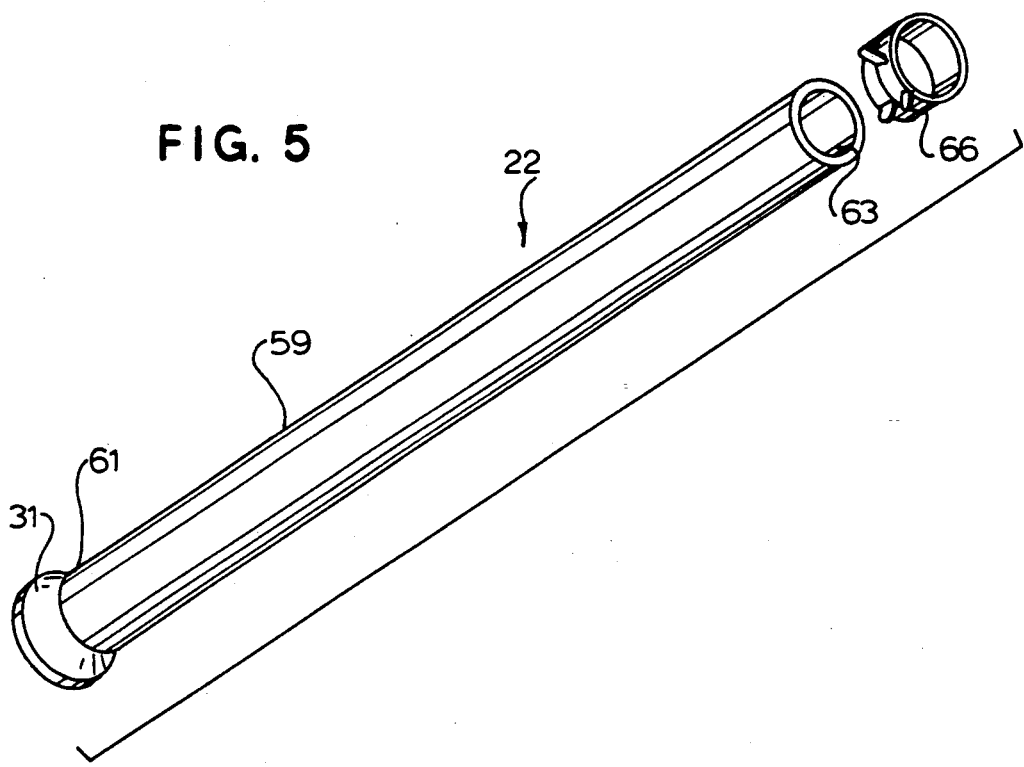
FIG. 5 is a perspective view of a bladder in accordance with the principles of the present invention.

Referring now to FIG. 5, there is illustrated a preferred embodiment of the elastomeric bladder 22 of the present invention. The elastomeric bladder 22 includes an elastic, generally cylindrical member 59 for defining an interior space which, in the unexpanded state, is of known interior cross sectional and axial dimensions. The elastomeric bladder 22 may be closed at the distal end 61. The bladder is open at the proximal end 63. The proximal end 63 is coaxially disposed around and in engagement with the access housing 16 as illustrated in FIG. 4. This seal is accomplished or enhanced by means of an annular clamp 66 extending therearound.

An annular flange or shoulder 68 is contained distal to the clamp 66 on the access housing 16. The flange 68 in cooperation with the clamp 66 prevents migration of the proximal end 63 of elastomeric bladder 22 in a distal direction due to elastic forces generated by the full elastomeric bladder 22 or by the axial prestress of the empty elastomeric bladder 22. Annular flange 68 comprises a proximal surface 70 and a distal surface 72 which extend radially outwardly from the access housing 16 and converge to form a relatively sharp angle at the radially outermost portion 74. The distal surface 72 is inclined outwardly from the surface of the access housing 16 at a more gradual angle than the proximal surface 70, thereby enhancing the securing function of annular flange 68. The size of the annular flange 68 generally is minimized so that it does not factor in the deflation characteristics of the elastomeric bladder 22.

The remaining length of the elastomeric bladder 22 is secured wrapped around the prestress member 20 in a helical manner. The elastomeric bladder 22 is prestressed around the prestress member 20 by applying an axial tension of approximately 30 to 100 percent elongation of the elastomeric bladder 22 while it is wrapped around the prestress member 20. Additionally, a distance (d) must be maintained between the unstressed elastomeric bladder 22 on the prestress member 20 to allow for expansion when liquid is introduced into the elastomeric bladder 22.

At the distal end of the prestress member 20 there is provided a slot 79 into which the distal end 61 of the elastomeric bladder 22 is placed. To effectuate this engagement, the distal end 61 of the elastomeric bladder 22 includes a flange 81 projecting radially outwardly which is secured into the slot 79. Alternatively, the elastomeric bladder 22 can be open ended at both ends and a securing clamp can be employed to secure the elastomeric bladder 22 to the prestress member 20 as well as close one open end. To assemble, the outwardly extending flange 81 is inserted into a secured relationship with the slot 79, the elastomeric bladder 22 is elongated and wrapped about the outer periphery of the prestress member 20, and the access housing 16 is inserted into the opening 14 provided at the proximal end of the casing 12. The access housing 16 can then be secured to the casing 12 by means such as an adhesive or sonic sealing or an appropriate mechanical attachment.

To use, the elastomeric bladder 22 is filled by a filling apparatus such as a syringe or pump having a cooperating member such as a luer connection to gain access to the fluid chamber defined in the interior of the bladder. The syringe or pump provides the liquid containing the beneficial agent at a sufficient pressure to push aside the valve band 42 and fill the elastomeric bladder 22. Because of the prestress of the elastomeric bladder 22 axially, filling expands the elastomeric bladder 22 radially while the axial length remains essentially unchanged.

Upon release of the pressure from the syringe, the resilient properties of the valve band 42 act in cooperation with the fluid pressure in the elastomeric bladder 22 to close traverse influent duct 39. This prevents escape of the liquid in the elastomeric bladder 22 via the inlet port 24.

The tubing 29 is first allowed to prime to eliminate any air contained in the system. The tubing 29 is then placed in fluid communication with the patient's venous system via a catheter.

Due to the axial prestressing of the elastomeric bladder 22, a pressure profile generated by deflation of the elastomeric bladder 22 will be substantially constant over the delivery volume as the terminal pressure spike of the bladder will be reduced. Additionally, the prestressing of the elastomeric bladder 22 ensures that substantially no air is dispersed within the deflated elastomeric bladder. The only air in the system will be contained in the lumen and tubing which air is easily primed out of the device. The prestressing further means only a minimal amount of the liquid having the beneficial agent will remain in the device after infusion.

Figure 6:
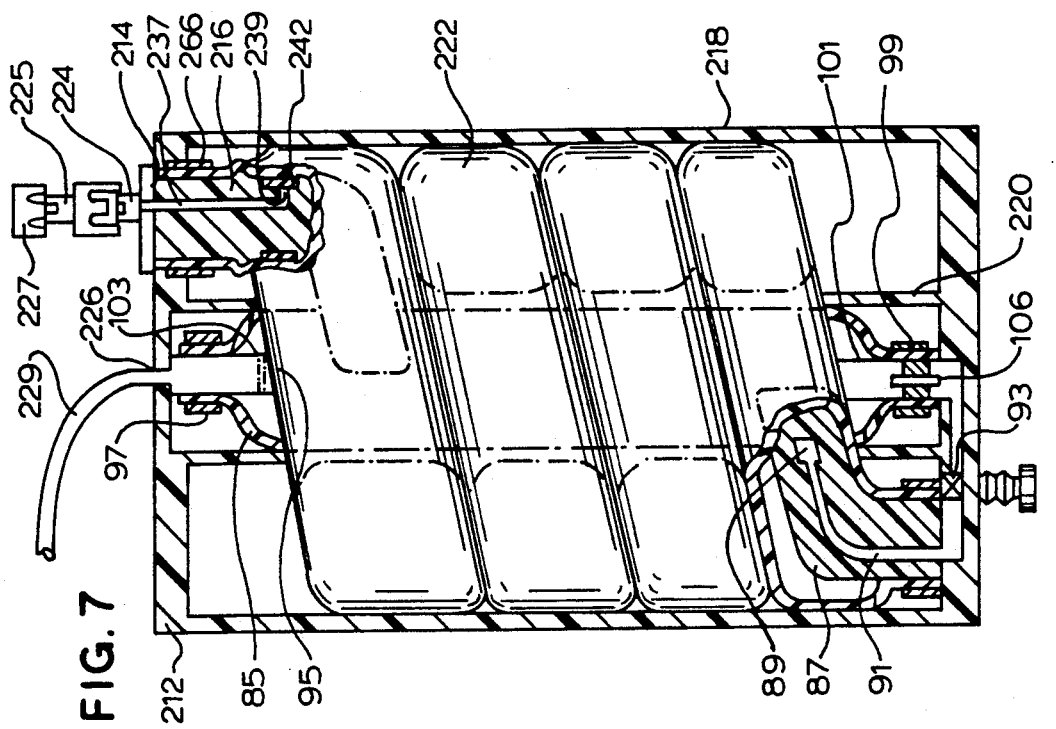
FIG. 6 is an elevational, partially sectional view of an additional embodiment of a device in accordance with the principles of the present invention with the elastomeric bladders in an unfilled state.
Figure 7:
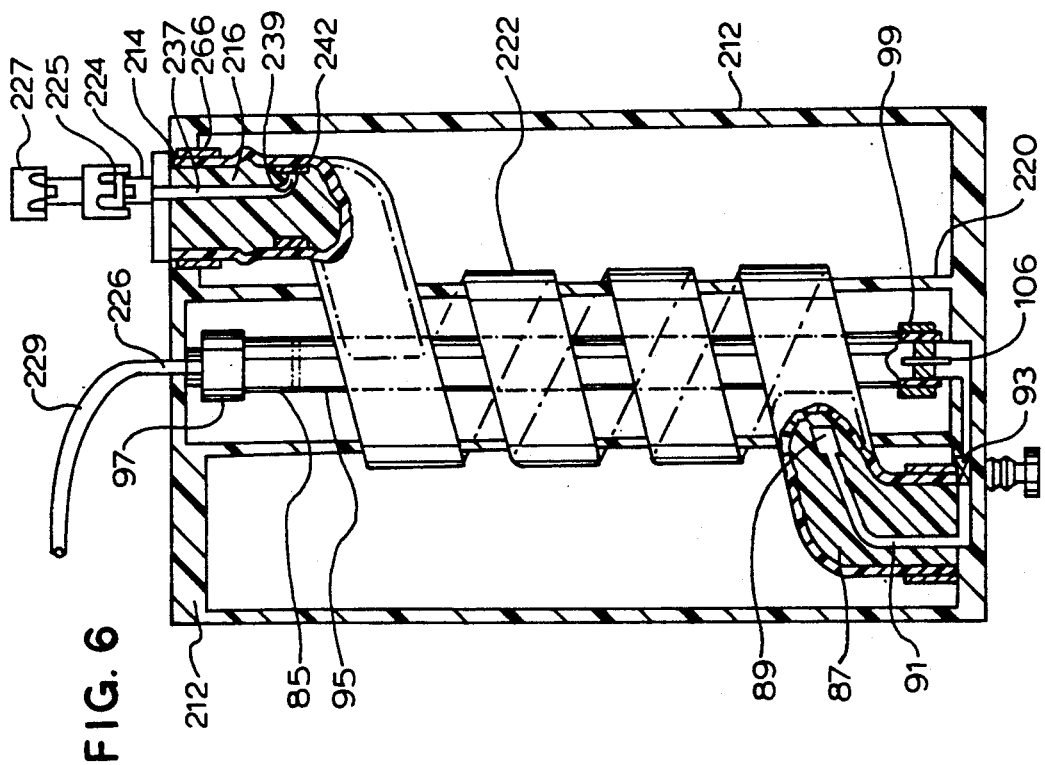
FIG. 7 is a elevational, partially sectional view of the device of FIG. 6 with the elastomeric bladders in a filled state.

Referring now to FIGS. 6 and 7, an additional embodiment of a device made in accordance with the principles of the present invention is seen in which like elements are depicted by 200 series of like numerals. This additional embodiment includes both a first elastomeric bladder 222 and a second elastomeric bladder 85. In this additional embodiment, once again access housing 216 is contained in the proximal opening 214 of casing 212. The access housing 216 includes a filling port 224 which is in fluid communication with the interior of the first bladder 222 by way of an influent lumen 237 and a transverse effluent duct 239. Backflow of the liquid in the first bladder 222 is again prevented by a one-way valve including an elastic valve band 242 disposed coaxially about the access housing 216 and in overlapping engagement with the transverse influent duct 239. The access housing 216 is again provided with an annular recess for receiving the valve band 242 so that the outside diameter of the valve band 242 is substantially the same as the diameter of the adjacent portions of the access housing 216.

In the access housing of this additional preferred embodiment, however, no exit port is provided. Rather, at the distal end of the first bladder a second access housing 87 is provided which defines an inlet 89 in fluid communication with the interior of the first bladder 222. An interal lumen 91 is provided in communication with the inlet 89 and the interior of the internal, generally cylindrical prestress member 220. A shut-off valve 93 is further provided in the lumen 91 to control access of fluid from the inlet 89 to the interior of the internal, generally cylindrical prestress member 220.

Contained within the internal, generally cylindrical prestress member 220 is a second prestress member 95. The second prestress member 95 preferably has a substantially uniform, circular cross-sectional shape throughout its entire length and extends axially along the first prestress member 220.

The second prestress member 95 has the second elastomeric bladder 85 contained thereon. The second elastomeric bladder 85 includes an open distal and an open proximal end. The second elastomeric bladder 85 includes an elastic, generally cylindrical member which defines an interior space which defines a fluid chamber and, in the unexpanded state, is of known interior cross-sectional and axial dimensions. The diameter of the second prestress member 95 is best provided slightly larger than the known interior diameter of the second elastomeric bladder 85.

The second elastomeric bladder 85 is coaxially disposed around and is engaged with the second prestress member 95. The open proximal and distal ends are secured to the second prestress member 95 in sealing engagement by means such as a proximal annular clamp 97 and a distal annular clamp 99 extending therearound.

The second prestress member 95 includes a distal inlet 101 and a proximal inlet 103, best seen in FIG. 7. The distal inlet 101 is in fluid communication with the interior lumen 91 leading to the access member inlet 89. The proximal inlet 103 is in fluid communication with the exit port 226.

The device contains a first flow regulator located between the second elastomeric bladder 85 and the patient. This first flow regulator can be contained in housing connected to the distal end of tubing 229 or can alternatively be contained between the proximal inlet 103 and the tubing 229 in the second prestress member 95. Contained within the internal lumen 91 is a second flow regulator 106. The second flow regulator 106 can be a glass capillary tube and can be formed substantially as described with regard to the first embodiment above.

To use this additional preferred embodiment, the first elastomeric bladder 222 is filled by a filling apparatus such as a syringe or pump. Again, the syringe or pump provides the liquid containing the beneficial agent at a sufficient pressure to push aside the valve band 242 and fill the first elastomeric bladder 222. When filling the first elastomeric bladder 222, the shut-off valve 93 in the interior lumen 91 is closed thereby preventing liquid from flowing into the second elastomeric bladder 85.

Upon release of the pressure from the syringe, the resilient properties of the valve band 242 act in cooperation with the fluid pressure in the first elastomeric bladder 222 to close traverse influent duct 239. This prevents escape of the liquid in the first elastomeric bladder 222 via the inlet port 224.

To prime, the shut off valve 93 is opened slightly which allows fluid from the first elastomeric bladder 222 to express air out of the system without filling the second elastomeric bladder 85. After priming is completed and the exterior tube 229 is connected to a patient's venous system via a catheter, the shut off valve 92 is fully opened which allows liquid from the first elastomeric bladder 222 to fill the second elastomeric bladder 85 through second flow regulator 106. Because second flow regulator 106 contained between the first elastomeric bladder 222 and the second elastomeric bladder 85 allows flow at a rate higher than that flow allowed by the first flow regulator contained between the second elastomeric bladder 85 and the patient, flow from the first elastomeric bladder 222 will supply both the patient with a flow of the liquid as well as fill the second elastomeric bladder 85. Thus, during this period, flow from the device increases at a rate determined by the pressure of the liquid in the first elastomeric bladder 222, the flow regulation of the first flow regulator, the resiliency of the second elastomeric bladder 85, and the flow regulation from the second flow regulator 106.

When fluid from the first elastomeric bladder 222 has filled the second elastomeric bladder 85, the pressure on the liquid being dispensed has increased to that of the pressure of the liquid in the first elastomeric bladder 222. This results in a substantially constant flow rate which depends on the pressure of the liquid in the first elastomeric bladder 222 and the first flow regulator 48. This flow rate continues until the first elastomeric bladder 222 empties at which time the flow decreases at a rate which depends on the pressure of the liquid in the second elastomeric bladder 85 and the second flow regulator 106.

Figure 8:
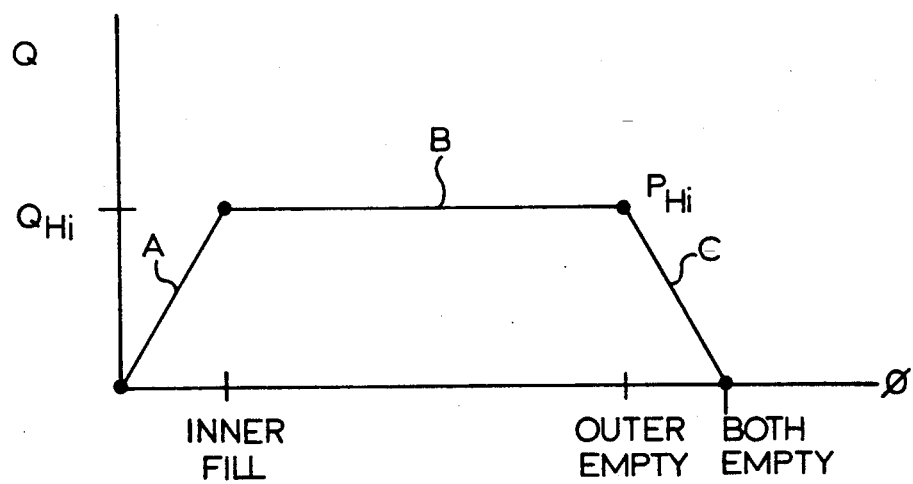
FIG. 8 is a diagram of the flow curve of the device of FIG. 6.

Thus, utilizing this combination the liquid can be infused into the patient starting with a ramp up flow rate (A), which increases to a constant flow rate (B), which then decreases to ramp down flow rate (C). (As seen in FIG. 8) As will be appreciated by those skilled in the art, if the shut off clamp is allowed to remain open during filling and both elastomeric bladders are allowed to fill, a dual rate infusion will be achieved with an initial bolus high rate of infusion followed by a second maintenance flow rate.

It should be understood that various changes and modifications to the preferred embodiment described herein will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. A device for infusing liquid into a patient comprising:
   an elongated resilient bladder defining a fluid chamber within the interior of the bladder and a filling port and an exit port in fluid communication with the interior of the bladder;
   housing defining a generally circular elongated prestress member, the housing further defining the filling port and the exit port;
   the elongated resilient bladder being wrapped about the exterior of the prestress member in a helical manner and in a contracted position such that the bladder is prestressed against the prestress member and the interior of the bladder is substantially empty of fluid when in the contracted position.

2. The device of claim 1 further wherein the elongated resilient bladder is wrapped about the exterior of the prestress member in a helical manner and in a contracted position under elongation to prestress the bladder.

3. The device of claim 1 wherein the elongated resilient bladder includes an open end secured to the housing which defines the fluid inlet and the fluid outlet and a closed end secured to the housing.

4. The device of claim 1 wherein the fluid inlet further includes a one-way valve.

5. The device of claim 1 further including a second elongated elastomeric bladder contained internally of the prestress member, the second elongated elastomeric bladder defining a second fluid chamber within the interior of the second bladder, the fluid chamber being in fluid communication with the first elastomeric bladder.

6. The device of claim 5 wherein the housing further defines a second prestress member contained within the fluid chamber of the second elastomeric bladder.

7. The device of claim 6 wherein the second prestress member extends throughout the entire length of the second elastomeric bladder.

8. The device of claim 6 wherein the second prestress member is generally cylindrical and has an external diameter which is larger than the internal diameter of an unstressed second elastomeric bladder.

9. A device for infusing liquid into a patient comprising:
   housing defining a first hollow prestress member and a second prestress member defined internally of the first prestress member, the housing further defining a filling port and an exit port;
   a first elongated elastomeric bladder defining a first fluid chamber within the interior of the bladder, the first fluid chamber being in fluid communication with the filling port, the first elongated elastomeric bladder being wound about the exterior of the first prestress member in a contracted position such that the first elongated elastomeric bladder is prestressed against the first prestress member and the interior of the first elongated elastomeric bladder is substantially empty of fluid when in the contracted position;
   a second elongated elastomeric bladder defining a second fluid chamber within the interior of the second elongated elastomeric bladder, the second prestress member contained within the second fluid chamber of the second elongated elastomeric bladder such that the second elongated elastomeric bladder is prestressed against the second prestress member and the interior of the second elongated elastomeric bladder is substantially empty of fluid when in a contracted position, the second elongated elastomeric bladder being in fluid communication with the exit port and the first fluid chamber of the first elongated elastomeric bladder.

10. The device of claim 9 further wherein the first elongated resilient bladder is wound about the exterior of the first prestress member in a contracted position under elongation to prestress the bladder.

11. The device of claim 9 wherein the fluid inlet further includes a one-way valve.

12. The device of claim 9 wherein the second prestress member extends throughout the entire length of the second elastomeric bladder.

13. The device of claim 9 wherein the second prestress member is generally cylindrical and has an external diameter which is larger than the internal diameter of an unstressed second elastomeric bladder.

* * * * *